United States Patent [19]

Padmanathan

[11] 4,065,477

[45] Dec. 27, 1977

[54] PROCESS FOR PREPARING HIGHLY PURE 1-NITROANTHRAQUINONE

[75] Inventor: Thurairajah Padmanathan, Piscataway, N.J.

[73] Assignee: American Cyanamid Company, Stamford, Conn.

[21] Appl. No.: 736,663

[22] Filed: Oct. 29, 1976

[51] Int. Cl.$^2$ .................. C07C 49/68; C09B 1/04
[52] U.S. Cl. ................. 260/369; 260/523 A; 260/524 N; 260/590 FB; 560/51
[58] Field of Search ......................... 260/369

[56] References Cited

U.S. PATENT DOCUMENTS

| 1,856,231 | 5/1932 | Stowell | 260/369 |
| 3,032,560 | 5/1962 | Dawsey | 260/369 |
| 3,416,257 | 3/1976 | Schaffner et al. | 260/369 |
| 3,932,474 | 1/1976 | Arzoumanidis et al. | 260/369 |

FOREIGN PATENT DOCUMENTS 535,451  1/1957  Canada .................. 260/369

OTHER PUBLICATIONS

Blakey et al., "Nitration and Bromination of 4 Methylbenzophenone", vol. 23, 1929, p. 129 in Chem. Abs.
Chardonnens L., "The Nitration of 4-CH$_3$benzophenone", in Chem. Abs. vol. 23, 1929, p. 4687.
Weiss et al., "Preparation of Acridone Derivatives", in Chem. Abs., 1929, p. 839, vol. 23.

Primary Examiner—Allen B. Curtis
Attorney, Agent, or Firm—John L. Sullivan

[57] ABSTRACT

1-Nitroanthraquinone is produced in highly pure form by a process comprising the steps of partially oxidizing 3-nitro-o-xylene (I) to 2-methyl-3-nitrobenzoic acid (II) converting II to 2-methyl-3-nitrobenzoyl halide (III), converting III to the novel intermediate 2-methyl-3-nitrobenzophenone (IV), oxidizing IV to 2-benzoyl-6-nitrobenzoic acid (V) and cyclizing V to 1-nitroanthraquinone.

3 Claims, No Drawings

PROCESS FOR PREPARING HIGHLY PURE 1-NITROANTHRAQUINONE

This invention pertains to a process for the preparation of 1-nitroanthraquinone and to a novel intermediate suitable for the preparation thereof. More particularly, this invention pertains to a process for preparing 1-nitroanthraquinone from 3-nitro-o-xylene via the novel intermediate 2-methyl-3-nitrobenzophenone.

The compound 1-nitroanthraquinone, and its reduction product 1-aminoanthraquinone, are important intermediates in the preparation of pigments, vat dyes, disperse dyes and acid dyes. Currently, 1-aminoanthraquinone is manufactured by either nitrating anthraquinone and reducing the nitration product, or sulfonating anthraquinone and aminating the sulfonation product.

The product obtained by the nitration process is accompanied by 2-nitroanthraquinone and 1,5-, 1,8-, 1,6-, and 1,7-dinitroanthraquinone, undesirable contaminants. In order to obtain high quality 1-aminoanthraquinone from this product, multiple purification steps are required after the nitration and reduction reactions.

The product obtained by the sulfonation process is contaminated by a mercury salt catalyst which is required in order to specifically sulfonate the 1-position of anthraquinone. All of the mercury salt catalyst must be recovered and reused to satisfy ecological and economic requirements. There is a need therefore for a process for the production of high purity 1-nitroanthraquinone which can be reduced to high purity 1-aminoanthraquinone.

I have discovered a novel process for the preparation of 1-nitroanthraquinone which comprises partially oxidizing 3-nitro-o-xylene (I) to 2-methyl-3-nitrobenzoic acid (II); converting II to the 2-methyl-3-nitrobenzoylhalide (III); converting III to the novel intermediate 2-methyl-3-nitrobenzophenone (IV); oxidizing IV to 2-benzoyl-6-nitrobenzoic acid (V), and cyclizing V to 1-nitroanthraquinone (VI), as shown in chart I.

In theory one could partially oxidize 3-nitro-o-xylene to 2-methyl-6-nitrobenzoic acid (VII), convert VII to a 2-methyl-6-nitrobenzoyl halide (VIII), convert VIII to 2-methyl-6-nitrobenzophenone (IX), oxidize IX to 2-benzoyl-3-nitrobenzoic acid (X) and cyclize the latter to 1-nitroanthraquinone. However, the conversion of VIII to IX is accompanied by side reactions which produce a black resinous unidentifiable product. Therefore, the preparation of 1-nitroanthraquinone (VI) by this route, as outlined in Chart II below, is not feasible.

CHART I

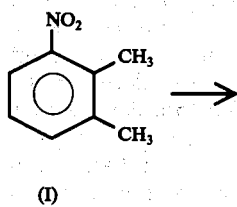
(I)

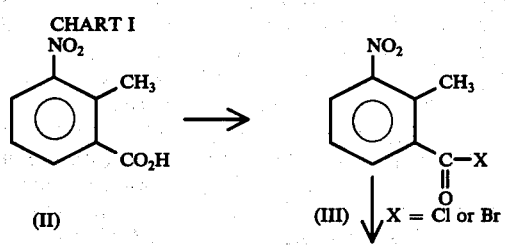
(II)     (III) X = Cl or Br

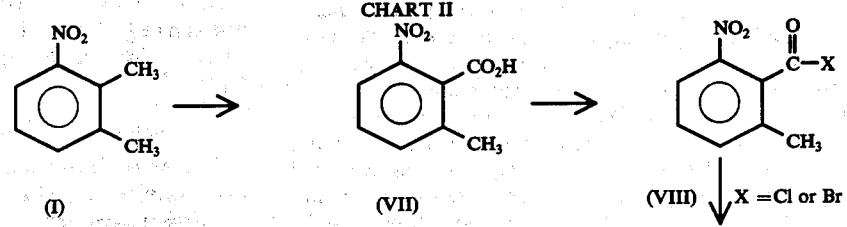
(VI)     (V)     (IV)

CHART II

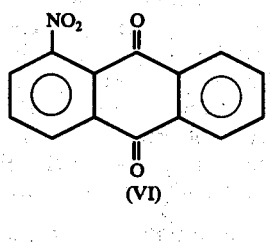
(I)

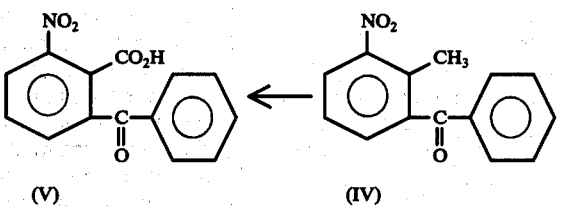
(VII)     (VIII) X = Cl or Br

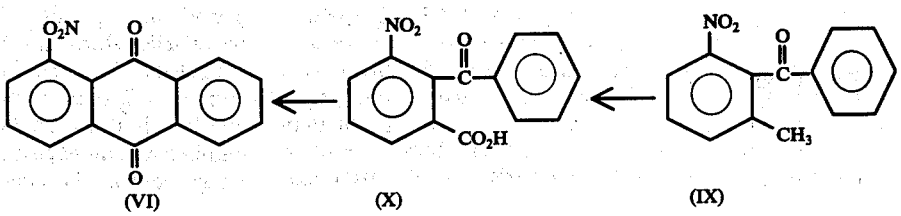
(VI)     (X)     (IX)

The advantages of the instant invention are as follows:

1. The product, 1-nitroanthraquinone, is obtained in an isomer-free state of purity and is convertible to high purity 1-aminoanthraquinone; and 2. The conversion of 3-nitro-o-xylene, a commercially available starting material, to the novel intermediate 2-methyl-3-nitrobenzophenone takes place in a relatively high overall yield.

The oxidation of 3-nitro-o-xylene (I) to 2-methyl-3-nitrobenzoic acid (II) is carried out by refluxing a solution of I in 40–55% by weight aqueous nitric acid for a period of 18–48 hours, preferably in 45–50% aqueous nitric acid for a period of about 24 hours. The solid precipitate which is obtained is predominantly the desired 2-methyl-3-nitrobenzoic acid. The crude product may be purified by dissolving it in an aqueous solution of a base such as sodium carbonate, sodium bicarbonate, sodium hydroxide, potassium hydroxide, and the like, and precipitating it by adding an inorganic acid thereto, such as hydrochloric, sulfuric and nitric acids. The product (II) is obtained in a yield of about 45–50% based on the 3-nitro-o-xylene consumed.

The conversion of 2-methyl-3-nitrobenzoic acid (II) to a 2-methyl-3-nitrobenzoyl halide (III) may be effected by reacting II with a suitable halogenating agent, such as phosphorus pentachloride, phosphorus pentabromide, thionyl chloride, and the like, preferably thionyl chloride, in a suitable inert solvent, such as dry benzene, at a temperature from room temperature to reflux until the reaction is complete and removing the solvent under reduced pressure. Preferably, II is converted to 2-methyl-3-nitrobenzoyl chloride by simply refluxing it in pure thionyl chloride for about 2–6 hours and removing the excess thionyl chloride under reduced pressure. The preferred 2-methyl-3-nitrobenzoyl chloride is obtained in yields of 95–100% of theoretical.

The conversion of the 2-methyl-3-nitrobenzoyl halide (III) to 2-methyl-3-nitrobenzophenone (IV) is carried out by stirring a solution of III in dry benzene in the presence of a suitable Friedel Crafts catalyst, such as aluminum chloride, trifluoromethane sulfonic acid, or the like, preferably aluminum chloride, at a temperature from room temperature to reflux temperature, until the reaction is completed. Preferably, III is dissolved in dry benzene containing about 2 moles of aluminum chloride per mole of III used, the reaction mixture is stirred at room temperature for about 2–3 hours, then heated at reflux for about 1–3 hours and cooled to room temperature. The reaction mixture is poured into a dilute aqueous mineral acid, preferably dilute hydrochloric acid, and the organic phase is separated, washed with aqueous sodium carbonate, dried and evaporated under reduced pressure to recover the desired novel intermediate (IV) in a yield about 95% of theoretical.

The conversion of 2-methyl-3-nitrobenzophenone (IV) to 2-benzoyl-6-nitrobenzoic acid (V) is carried out by oxidizing IV with a 15–25% aqueous solution of nitric acid in a sealed reaction vessel under autogenous pressure at 125°–165° C for a period of about 18–48 hours; preferably the reaction is carried out with a 20% aqueous solution of nitric acid at 145°–155° C for a period of about 20–24 hours. The reaction mixture is then cooled to room temperature, the reaction vessel is vented to the atmosphere and the contents discharged as a slurry. The product (V) is recovered by filtration in a yield about 40–50% of the theoretical. Identification of the product is made by comparison of its infrared absorption spectrum to that of an authentic sample (see Chase et al, J.C.S. [1952], page 567).

The cyclization of 2-benzoyl-6-nitrobenzoic acid (V) to 1-nitroanthraquinone (VI) is effected by adding V to a suitable inorganic acid, such as concentrated sulfuric acid or polyphosphoric acid, heating the reaction mixture at an elevated temperature to effect cyclization to VI, preferably at 100°–110° C, for a period of 1–3 hours, cooling the reaction mixture to room temperature, pouring the reaction mixture into water and recovering the solid by filtration. The filter cake is successively washed with a dilute aqueous solution of sodium carbonate and water, and dried to obtain VI in a yield which is 85% of theoretical.

The reduction of 1-nitroanthraquinone may be effected by methods which are well-known in the art, such as by heating with aqueous sodium sulfide, in yields of 90–95% of theoretical.

The following example is illustrative of the process of this invention. All percentages mentioned in the example are by weight unless otherwise indicated.

EXAMPLE

A. Preparation of 2-Methyl-3-Nitrobenzoic Acid

A mixture of 3-nitro-o-xylene (15.1 grams; 0.10 mole) in a 51.6% aqueous solution of nitric acid, prepared by gradually adding 75 mls. of concentrated nitric acid to 38 mls. of water, was stirred and heated at reflux for 24 hours and then cooled to room temperature. The reaction mixture was filtered to separate the precipitate. The filtrate was extracted with chloroform, allowed to settle and the chloroform layer separated therefrom. The chloroform layer was extracted with aqueous sodium carbonate and the aqueous phase was separated from the organic phase. The organic phase was then concentrated to dryness to recover unreacted 3-nitro-o-xylene (6.5 grams; 0.043 mole).

The solid precipitate was added to the aqueous phase and the resulting mixture was stirred until the solid dissolved completely. The resulting solution was then acidified by adding concentrated hydrochloric acid thereto. The resulting white precipitate was separated by filtration, washed with water and dried to obtain 4.8 grams of product which was identified by its infrared spectrum as 2-methyl-3-nitrobenzoic acid. The yield based on 3-nitro-o-xylene consumed was 46.6%.

B. Preparation of 2-Methyl-3-Nitrobenzoyl Chloride

A mixture of 2-methyl-3-nitrobenzoic acid (9.2 grams; 0.05 mole) and 15 mls. of thionyl chloride was heated at reflux for 6 hours. The excess thionyl chloride was removed by distillation to obtain 2-methyl-3-nitrobenzoyl chloride (9.5 grams; 95% yield; m.p. 68°–70° C).

C. Preparation of 2-Methyl-3-Nitrobenzophenone

2-Methyl-3-nitrobenzoyl chloride (9.98 grams; 0.05 mole) was dissolved in 35 mls. of dry benzene and the solution was added to a slurry of aluminum chloride (13.3 grams; 0.10 mole) in 40 mls. of dry benzene over a period of 10 minutes. The resulting reaction mixture was stirred at room temperature for 26 ½ hours, then heated at reflux for 2 hours and cooled to room temperature. The cooled reaction mixture was poured into 200 mls. of dilute hydrochloric acid, stirred for about 15 minutes and allowed to settle. The organic phase was separated and the aqueous phase was back extracted with 200 mls. of benzene. The benzene layer was separated and combined with the organic phase and the combined solution was washed successively with water, a dilute aqueous solution of sodium carbonate, and water. The organic phase was dried over anhydrous sodium sulfate, filtered, concentrated and distilled to obtain 2-methyl-3-nitrobenzophenone (11.45 grams; 95% yield; b.p. 183° C at 2 mm; m.p. 42° C after recrystallization from petroleum ether).

Calculated for $C_{14}H_{11}NO_3$ (percent by weight): C, 69.70; H, 4.59; N, 5.8. Found: C, 69.50; H, 4,62; N, 5.54.

D. Preparation of 2-Benzoyl-6-Nitrobenzoic Acid

A mixture of 2-methyl-3-nitrobenzophenone (24.1 grams; 0.10 mole) and a 19.2% aqueous solution of nitric acid, prepared by adding 20 mls. of concentrated nitric acid to 75 mls. of water and mixing thoroughly, was stirred in a sealed autoclave at 150° C for a period of 24 hours. The autoclave was then cooled to room temperature, vented and the contents discharged. The reaction mixture was extracted with 350 mls. of chloroform and the chloroform extract was separated from the aqueous phase and concentrated to a volume of 150 mls. The chloroform concentrate was washed with a dilute aqueous solutin of sodium carbonate and the aqueous layer was separated and acidified by adding dilute hydrochloric acid thereto. The resulting slurry was allowed to stand at room temperature for several hours and the solid was separated by filtration and dried. The product 2-benzoyl-6-notrobenzoic acid (14.1 grams; 52% yield) was identified by comparison of its infrared spectrum with that of an authentic sample.

E. Preparation of 1-Nitroanthraquinone

A solution of 2-benzoyl-6-nitrobenzoic acid (2.0 grams; 0.0074 mole) in 10 mls. of concentrated sulfuric acid (99.5% by weight) was stirred at 100° C for 3 hours, then cooled to room temperature and poured into a mixture of ice and water. The resulting mixture was filtered to recover the precipitated solids. The filter cake was then washed successively with a dilute aqueous solution of sodium carbonate and water, and dried to obtain 1-nitroanthraquinone (1.59 grams; 85% yield). The product was identified by comparison of its vapor phase chromatographic spectrum with that of an authentic sample.

I claim:

1. A process for preparing 1-nitroanthraquinone comprising the steps of:
    1. oxidizing 3-nitro-o-xylene to form 2-methyl-3-nitrobenzoic acid,
    2. converting said 2-methyl-3-nitrobenzoic acid to a 2-methyl-3-nitrobenzoyl halide,
    3. reacting said 2-methyl-3-nitrobenzoyl halide with benzene in the presence of a suitable Friedel Crafts catalyst to form 2-methyl-3nitrobenzophenone,
    4. oxidizing said 2-methyl-3-nitrobenzophenone to form 2-benzoyl-6-nitrobenzoic acid, and
    5. cyclizing said 2-benzoyl-6-nitrobenzoic acid in a sutiable inorganic acid to form 1-nitroanthraquinone and recovering the same therefrom.

2. A process for preparing 1-nitroanthraquinone comprising the steps of:
    1. oxidizing 3-nitro-o-xylene in 40–55% by weight aqueous nitric acid at reflux temperature for 18–48 hours to form 2-methyl-3-nitrobenzoic acid,
    2. reacting said 2-methyl-3-nitrobenzoic with thionyl chloride to form 2-methyl-3-nitrobenzoyl chloride,
    3. reacting one mole of said 2-methyl-3-nitrobenzoyl chloride with anhydrous benzene in the presence of two moles of aluminum chloride to form 2-methyl-3nitrobenzophenone,
    4. oxidizing said 2-methyl-3nitrobenzophenone in 15–25% aqueous nitric acid under autogenous pressure at a temperature of 125°–165° C for a period of 18–48 hours to form 2-benzoyl-6-nitrobenzoic acid, and
    5. cyclizing said 2-benzoyl-6-nitrobenzoic acid in concentrated sulfuric acid to form 1-nitroanthraquinone and recovering the same therefrom.

3. A process for preparing 1-nitroanthraquinone comprising the steps of:
    1. oxidizing 3-nitro-o-xylene in 50% aqueous nitric acid at reflux temperature for a period of 24 hours to form 2-methyl-3-nitrobenzoic acid,
    2. reacting said 2-methyl-3-nitrobenzoic acid in refluxing thionyl chloride to form 2-methyl-3-nitrobenzoyl chloride,
    3. reacting one mole of said 2-methyl-3-nitrobenzoyl chloride in refluxing benzene in the presence of two moles of aluminum chloride for a period of 2–3 hours to form 2-methyl-3-nitrobenzophenone,
    4. oxidizing said 2-methyl-3-nitrobenzophenone in 20% aqueous nitric acid for a period of 20 –24 hours at 145°–155° C to form 2-benzoyl-6-nitrobenzoic acid, and
    5. cyclizing said 2-benzoyl-6-nitrobenzoic acid in concentrated sulfuric acid at a temperature of 100°–110° C for a period of 1–3 hours to form 1-nitroanthraquinone and recovering the same therefrom.

* * * * *